US009617351B2

(12) United States Patent
Petermann et al.

(10) Patent No.: US 9,617,351 B2
(45) Date of Patent: *Apr. 11, 2017

(54) ESTERIFIED CELLULOSE ETHERS OF VERY LOW VISCOSITY

(71) Applicant: Dow Global Technologies LLC, Midland, MI (US)

(72) Inventors: Oliver Petermann, Hamburg (DE); Robert B. Appell, Midland, MI (US); Meinolf Brackhagen, Walsrode (DE)

(73) Assignee: Dow Global Technologies LLC

( * ) Notice: Subject to any disclaimer, the term of this patent is extended or adjusted under 35 U.S.C. 154(b) by 0 days.

This patent is subject to a terminal disclaimer.

(21) Appl. No.: 14/766,786

(22) PCT Filed: Feb. 28, 2014

(86) PCT No.: PCT/US2014/019266
§ 371 (c)(1),
(2) Date: Aug. 10, 2015

(87) PCT Pub. No.: WO2014/137778
PCT Pub. Date: Sep. 12, 2014

(65) Prior Publication Data
US 2015/0376299 A1   Dec. 31, 2015

Related U.S. Application Data

(60) Provisional application No. 61/774,161, filed on Mar. 7, 2013.

(51) Int. Cl.
| | |
|---|---|
| *C08B 13/00* | (2006.01) |
| *A61K 47/38* | (2006.01) |
| *A61K 9/14* | (2006.01) |
| *C08B 11/20* | (2006.01) |
| *A61K 9/28* | (2006.01) |
| *A61K 9/48* | (2006.01) |

(52) U.S. Cl.
CPC .............. *C08B 13/00* (2013.01); *A61K 9/146* (2013.01); *A61K 47/38* (2013.01); *C08B 11/20* (2013.01); *A61K 9/2866* (2013.01); *A61K 9/4816* (2013.01)

(58) Field of Classification Search
CPC ...... A61K 47/38; A61K 9/146; A61K 9/4816; A61K 9/2866; C08B 13/00; C08B 11/20
USPC ............ 424/422, 480, 494; 514/781; 536/64
See application file for complete search history.

(56) References Cited

U.S. PATENT DOCUMENTS

| | | |
|---|---|---|
| 3,712,886 A | 1/1973 | Koyanagi et al. |
| 4,226,981 A * | 10/1980 | Onda .................. A61K 9/2866 |
| | | 424/480 |
| 4,365,060 A | 12/1982 | Onda et al. |
| 5,776,501 A | 7/1998 | Kokubo et al. |
| 2003/0219489 A1 | 11/2003 | Curatolo et al. |
| 2004/0152886 A1 | 8/2004 | Cho et al. |
| 2004/0242862 A1 | 12/2004 | Hammes |

FOREIGN PATENT DOCUMENTS

| | | | |
|---|---|---|---|
| EP | 0219426 A2 * | 4/1987 | ............. C08B 13/00 |
| EP | 08722333 A1 | 10/1998 | |
| JP | 2010241696 | 10/2010 | |
| WO | 02085949 A1 | 10/2002 | |
| WO | 03097616 A1 | 11/2003 | |
| WO | 2004014342 A1 | 2/2004 | |
| WO | 2005115330 A2 | 12/2005 | |
| WO | 2009061815 A1 | 5/2009 | |
| WO | 2009061821 A2 | 5/2009 | |
| WO | 2009070744 A1 | 6/2009 | |
| WO | 2011159626 A1 | 12/2011 | |
| WO | WO 2011/159626 A1 * | 12/2011 | ............. A61K 47/38 |
| WO | 2013154607 A1 | 10/2013 | |
| WO | 2014031418 A1 | 2/2014 | |
| WO | 2014031419 A1 | 2/2014 | |
| WO | 2014031422 A1 | 2/2014 | |

OTHER PUBLICATIONS

Chen, Characterization of Hypromellose Acetate Succinate by Size Exclusion Chromatography (SEC) Using Viscotek Triple Detector, International Journal of Polymer Anal. Charact., vol. 14, 2009, pp. 617-630.
Keary, Characterization of METHOCEL cellulose ethers by aqueous SEC with multiple detectors, Carbohydrate Polymers, vol. 45, 2001, pp. 293-303.
Breitenbach, Melt extrusion: from process to drug delivery technology, European Journal of Pharmaceutics and Biopharmaceutics, vol. 54, 2002, pp. 107-117.
Chen, et al., Absolute molecular weight determination of hypromellose acetate succinate by size exclusion chromatography: Use of a multi angle laser light scattering detector and a mixed solvent, Journal of Pharmaceutical and Biomedical Analysis, vol. 56, 2011, pp. 743-748.
Friesen, et al., Hydroxypropyl Methylcellulose Acetate Succinate-Based Spray-Dried Dispersions: An Overview, Molecular Pharmaceutics, vol. 5, No. 6, 2008, pp. 1003-1019.

(Continued)

*Primary Examiner* — Ganapathy Krishnan

(57) ABSTRACT

An esterified cellulose ether which comprises (i) aliphatic monovalent acyl groups or (ii) groups of the formula —C(O)—R—COOA, wherein R is a divalent aliphatic or aromatic hydrocarbon group and A is hydrogen or a cation, or (iii) a combination of aliphatic monovalent acyl groups and groups of the formula —C(O)—R—COOA, and which has a) a viscosity of from 1.2 to 1.8 mPaos, measured as a 2.0 wt % solution of the esterified cellulose ether in 0.43 wt % aqueous NaOH at 20° C., or b) a viscosity of up to 5 mPa·s, measured as a 10 wt % solution of the esterified cellulose ether in acetone at 20° C., or c) a combination of the viscosities of a) and b), is useful for preparing solid dispersions comprising drugs.

13 Claims, No Drawings

(56) References Cited

OTHER PUBLICATIONS

Curatolo, et al., Utility of Hydroxypropylmethylcellulose Acetate Succinate (HPMCAS) for Initiation and Maintenance of Drug Supersaturation in the GI Milieu, Pharmaceutical Research, vol. 26, No. 6, 2009, pp. 1419-1431.
Feng, et al., Process Induced Disorder in Crystalline Materials: Differentiating Defective Crystals from the Amorphous Form of Griseofulvin, Journal of Pharmaceutical Sciences, vol. 97, No. 8. 2008. pp. 3207-3221.

\* cited by examiner

ESTERIFIED CELLULOSE ETHERS OF VERY LOW VISCOSITY

FIELD

This invention concerns novel esterified cellulose ethers, solid dispersions of an active ingredient in such esterified cellulose ether, as well as liquid compositions, coated dosage forms and capsules comprising such esterified cellulose ether.

INTRODUCTION

Esters of cellulose ethers, their uses and processes for preparing them are generally known in the art. Known methods of producing cellulose ether-esters include the reaction of a cellulose ether with an aliphatic monocarboxylic acid anhydride or a dicarboxylic acid anhydride or a combination thereof, for example as described in U.S. Pat. Nos. 4,226,981 and 4,365,060.

Various known esterified cellulose ethers are useful as enteric polymers for pharmaceutical dosage forms, such as methylcellulose phthalate, hydroxypropyl methylcellulose phthalate, methylcellulose succinate, or hydroxypropyl methylcellulose succinate. Dosage forms coated with such polymers protect the drug from inactivation or degradation in the acidic environment or prevent irritation of the stomach by the drug. U.S. Pat. No. 4,365,060 discloses enterosoluble capsules which are said to have excellent enterosolubility behavior.

U.S. Pat. No. 5,776,501 teaches the usage of a water-soluble cellulose ether having a viscosity of 3 to 10 cp (mPa·s), determined as a 2% by weight aqueous solution. If the viscosity is less than 3 cp, the finally obtained coating film for solid enteric pharmaceutical preparations is insufficient in strength, while if it exceeds 10 cp, the viscosity observed when it is dissolved in a solvent to carry out a substitution reaction becomes extremely high.

US Patent Application Publication No. 2004/0152886 discloses the production of hydroxypropyl methylcellulose phthalate starting from hydroxypropyl methylcellulose having a viscosity of 3 to 20 cp, measured as a 2 wt. % aqueous solution.

International patent applications WO 2005/115330 and WO 2011/159626 disclose the preparation of hydroxypropyl methylcellulose acetate succinate (HPMCAS). HPMC having an apparent viscosity of 2.4 to 3.6 cp is recommended as a starting material. Alternatively, a HPMC starting material of 600 to 60,000 Daltons, preferably 3000 to 50,000 Daltons, more preferably 6,000 to 30,000 Daltons is recommended. According to Keary [Keary, C. M.; Carbohydrate Polymers 45 (2001) 293-303, Tables 7 and 8] HPMC having a weight average molecular weight of about 85-100 kDa has a viscosity of about 50 mPaxs, determined as a 2% by weight aqueous solution.

A large number of presently known drugs have a low solubility in water, so that complex techniques are required to prepare a dosage form. One known method includes dissolving such drug together with a pharmaceutically acceptable water-soluble polymer, such as an esterified cellulose ether, in an organic solvent that is optionally blended with water, and to spray-dry the solution. The esterified cellulose ether is aimed at reducing the crystallinity of the drug, thereby minimizing the activation energy necessary for the dissolution of the drug, as well as establishing hydrophilic conditions around the drug molecules, thereby improving the solubility of the drug itself to increase its bioavailability, i.e., its in vivo absorption by an individual upon ingestion.

Unfortunately, the known esterified cellulose ethers often cannot be efficiently used in spray-drying operations. When known esterified cellulose ethers are dissolved at a high concentration in an organic solvent, such as a concentration of 7-10 weight percent, and such solution is combined with a drug and spray-dried, the resulting solution has a high viscosity, is difficult to be spray-dried and tends to clog the spray-drying device. When a highly diluted solution is utilized, an unduly high amount of organic solvent has to be evaporated. Similar problems occur when esterified cellulose ethers are dissolved in organic solvents and used for coating purposes, such as tablet coatings.

Accordingly, it would be highly desirable to find new esterified cellulose ethers which can be efficiently used in spray-drying and coating processes. It would be particularly desirable to find such new esterified cellulose ethers which are suitable for improving the solubility of drugs.

SUMMARY

One aspect of the present invention is an esterified cellulose ether which comprises (i) aliphatic monovalent acyl groups or (ii) groups of the formula —C(O)—R—COOA, wherein R is a divalent aliphatic or aromatic hydrocarbon group and A is hydrogen or a cation, or (iii) a combination of aliphatic monovalent acyl groups and groups of the formula —C(O)—R—COOA, wherein the esterified cellulose ether has a) a viscosity of from 1.2 to 1.8 mPa·s, measured as a 2.0 wt % solution of the esterified cellulose ether in 0.43 wt % aqueous NaOH at 20° C., or b) a viscosity of up to 5 mPa·s, measured as a 10 wt % solution of the esterified cellulose ether in acetone at 20° C., or c) a combination of the viscosities of a) and b).

Another aspect of the present invention is a composition which comprises a liquid diluent and at least one above-described esterified cellulose ether.

Yet another aspect of the present invention is a solid dispersion of at least one active ingredient in at least one above-described esterified cellulose ether.

Yet another aspect of the present invention is a dosage form which is coated with at least one above-described esterified cellulose ether.

Yet another aspect of the present invention is a capsule shell which comprises at least one above-described esterified cellulose ether.

Yet another aspect of the present invention is a process for producing an esterified cellulose ether wherein a cellulose ether having a viscosity of from 1.2 to 1.8 mPa·s, measured as a 2 wt.-% solution in water at 20° C., is esterified with (i) an aliphatic monocarboxylic acid anhydride or (ii) a dicarboxylic acid anhydride or (iii) a combination of an aliphatic monocarboxylic acid anhydride and a dicarboxylic acid anhydride.

DESCRIPTION OF EMBODIMENTS

The esterified cellulose ether has a cellulose backbone having β-1,4 glycosidically bound D-glucopyranose repeating units, designated as anhydroglucose units in the context of this invention. The esterified cellulose ether preferably is an esterified alkyl cellulose, hydroxyalkyl cellulose or hydroxyalkyl alkylcellulose. This means that in the esterified cellulose ether of the present invention, at least a part of the hydroxyl groups of the anhydroglucose units are substituted by alkoxyl groups or hydroxyalkoxyl groups or a combination of alkoxyl and hydroxyalkoxyl groups. The hydroxyalkoxyl groups are typically hydroxymethoxyl, hydroxyethoxyl and/or hydroxypropoxyl groups. Hydroxyethoxyl and/or hydroxypropoxyl groups are preferred. Typically one or two kinds of hydroxyalkoxyl groups are present in the esterified cellulose ether. Preferably a single kind of hydroxyalkoxyl group, more preferably hydroxypropoxyl, is present. The alkoxyl groups are typically methoxyl, ethoxyl and/or propoxyl groups. Methoxyl groups are preferred. Illustrative of the above-defined esterified cellulose ethers are esterified alkylcelluloses, such as esterified methylcelluloses, ethylcelluloses, and propylcelluloses; esterified hydroxyalkylcelluloses, such as esterified hydroxyethylcelluloses, hydroxypropylcelluloses, and hydroxybutylcelluloses; and esterified hydroxyalkyl alkylcelluloses, such as esterified hydroxyethyl methylcelluloses, hydroxymethyl ethylcelluloses, ethyl hydroxyethylcelluloses, hydroxypropyl methylcelluloses, hydroxypropyl ethylcelluloses, hydroxybutyl methylcelluloses, and hydroxybutyl ethylcelluloses; and those having two or more hydroxyalkyl groups, such as esterified hydroxyethylhydroxypropyl methylcelluloses. Most preferably, the esterified cellulose ether is an esterified hydroxyalkyl methylcellulose, such as hydroxypropyl methylcellulose.

The degree of the substitution of hydroxyl groups of the anhydroglucose units by hydroxyalkoxyl groups is expressed by the molar substitution of hydroxyalkoxyl groups, the MS(hydroxyalkoxyl). The MS(hydroxyalkoxyl) is the average number of moles of hydroxyalkoxyl groups per anhydroglucose unit in the esterified cellulose ether. It is to be understood that during the hydroxyalkylation reaction the hydroxyl group of a hydroxyalkoxyl group bound to the cellulose backbone can be further etherified by an alkylating agent, e.g. a methylating agent, and/or a hydroxyalkylating agent. Multiple subsequent hydroxyalkylation etherification reactions with respect to the same carbon atom position of an anhydroglucose unit yields a side chain, wherein multiple hydroxyalkoxyl groups are covalently bound to each other by ether bonds, each side chain as a whole forming a hydroxyalkoxyl substituent to the cellulose backbone.

The term "hydroxyalkoxyl groups" thus has to be interpreted in the context of the MS(hydroxyalkoxyl) as referring to the hydroxyalkoxyl groups as the constituting units of hydroxyalkoxyl substituents, which either comprise a single hydroxyalkoxyl group or a side chain as outlined above, wherein two or more hydroxyalkoxyl units are covalently bound to each other by ether bonding. Within this definition it is not important whether the terminal hydroxyl group of a hydroxyalkoxyl substituent is further alkylated or not; both alkylated and non-alkylated hydroxyalkoxyl substituents are included for the determination of MS(hydroxyalkoxyl). The esterified cellulose ether of the invention generally has a molar substitution of hydroxyalkoxyl groups in the range 0.05 to 1.00, preferably 0.08 to 0.90, more preferably 0.12 to 0.70, most preferably 0.15 to 0.60, and particularly 0.21 to 0.50.

The average number of hydroxyl groups substituted by alkoxyl groups, such as methoxyl groups, per anhydroglucose unit, is designated as the degree of substitution of alkoxyl groups, DS(alkoxyl). In the above-given definition of DS, the term "hydroxyl groups substituted by alkoxyl groups" is to be construed within the present invention to include not only alkylated hydroxyl groups directly bound to the carbon atoms of the cellulose backbone, but also alkylated hydroxyl groups of hydroxyalkoxyl substituents bound to the cellulose backbone. The esterified cellulose ethers according to this invention preferably have a DS(alkoxyl) in the range of 1.0 to 2.5, more preferably from 1.1 to 2.4, even more preferably from 1.2 to 2.2, most preferably from 1.6 to 2.05, and particularly from 1.7 to 2.05.

Most preferably the esterified cellulose ether is an esterified hydroxypropyl methylcellulose having a DS(methoxyl) within the ranges indicated above for DS(alkoxyl) and an MS(hydroxypropoxyl) within the ranges indicated above for MS(hydroxyalkoxyl).

The esterified cellulose ether of the present invention has (i) aliphatic monovalent acyl groups or (ii) groups of the formula —C(O)—R—COOA, wherein R is a divalent aliphatic or aromatic hydrocarbon group and A is hydrogen or a cation, or (iii) a combination of aliphatic monovalent acyl groups and groups of the formula —C(O)—R—COOA. The cation preferably is an ammonium cation, such as $NH_4^+$ or an alkali metal ion, such as the sodium or potassium ion, more preferably the sodium ion. Most preferably, A is hydrogen.

The aliphatic monovalent acyl groups are preferably selected from the group consisting of acetyl, propionyl, and butyryl, such as n-butyryl or i-butyryl.

Preferred groups of the formula —C(O)—R—COOA are —C(O)—CH$_2$—CH$_2$—COOA, such as —C(O)—CH$_2$—CH$_2$—COOH or —C(O)—CH$_2$—CH$_2$—COO$^-$Na$^+$, C(O)—CH=CH—COOA, such as —C(O)—CH=CH—COOH or —C(O)—CH=CH—COO$^-$Na$^+$, or —C(O)—C$_6$H$_4$—COOA, such as —C(O)—C$_6$H$_4$—COOH or —C(O)—C$_6$H$_4$—COO$^-$Na$^+$.

In the groups of formula —C(O)—C$_6$H$_4$—COOA the carbonyl group and the carboxylic group are preferably arranged in ortho-positions.

Preferred esterified cellulose ethers are i) HPMCXY, wherein HPMC is hydroxypropyl methyl cellulose, X is A (acetate), or X is B (butyrate) or X is Pr (propionate) and Y is S (succinate), or Y is P (phthalate) or Y is M (maleate), such as hydroxypropyl methyl cellulose acetate phthalate (HPMCAP), hydroxypropyl methyl cellulose acetate maleate (HPMCAM), or hydroxypropyl methylcellulose acetate succinate (HPMCAS), or ii) hydroxypropyl methyl cellulose phthalate (HPMCP), hydroxypropyl cellulose acetate succinate (HPCAS), hydroxybutyl methyl cellulose propionate succinate (HBMCPrS), hydroxyethyl hydroxypropyl cellulose propionate succinate (HEHPCPrS); and methyl cellulose acetate succinate (MCAS).

Hydroxypropyl methylcellulose acetate succinate (HPMCAS) is the most preferred esterified cellulose ether.

The esterified cellulose ethers generally have a degree of substitution of aliphatic monovalent acyl groups, such as acetyl, propionyl, or butyryl groups, of 0 to 1.75, preferably of 0.05 to 1.50, more preferably of 0.10 to 1.25, and most preferably of 0.20 to 1.00.

The esterified cellulose ethers generally have a degree of substitution of groups of formula —C(O)—R—COOA, such as succinoyl, of 0.05 to 1.6, preferably of 0.05 to 1.30, more preferably of 0.05 to 1.00, and most preferably of 0.10 to 0.70 or even 0.10 to 0.60.

The sum of i) the degree of substitution of aliphatic monovalent acyl groups and ii) the degree of substitution of groups of formula —C(O)—R—COOA is generally from 0.05 to 2.0, preferably from 0.10 to 1.4, more preferably from 0.20 to 1.15, most preferably from 0.30 to 1.10 and particularly from 0.40 to 1.00.

The content of the acetate and succinate ester groups is determined according to "Hypromellose Acetate Succinate", United States Pharmacopeia and National Formulary, NF 29, pp. 1548-1550. Reported values are corrected for volatiles (determined as described in section "loss on drying" in the above HPMCAS monograph). The method may be used in analogue manner to determine the content of propionyl, butyryl, phthalyl and other ester groups.

The content of ether groups in the esterified cellulose ether is determined in the same manner as described for "Hypromellose", United States Pharmacopeia and National Formulary, USP 35, pp 3467-3469.

The contents of ether and ester groups obtained by the above analyses are converted to DS and MS values of individual substituents according to the formulas below. The formulas may be used in analogue manner to determine the DS and MS of substituents of other cellulose ether esters.

$$\% \text{ cellulose } backbone = 100 - \left(\%MeO * \frac{M(OCH_3) - M(OH)}{M(OCH_3)}\right) -$$
$$\left(\%HPO * \frac{M(OCH_2CH(OH)CH_3) - M(OH)}{M(OCH_2CH(OH)CH_3)}\right) -$$
$$\left(\%\text{Acetyl} * \frac{M(COCH_3) - M(H)}{M(COCH_3)}\right) -$$
$$\left(\%Succinoyl * \frac{M(COC_2H_4COOH) - M(H)}{M(COC_2H_4COOH)}\right)$$

$$DS(Me) = \frac{\frac{\%MeO}{M(OCH_3)}}{\frac{\%\text{cellulose } backbone}{M(AGU)}}$$

$$MS(HP) = \frac{\frac{\%HPO}{M(HPO)}}{\frac{\%\text{cellulose } backbone}{M(AGU)}}$$

$$DS(\text{Acetyl}) = \frac{\frac{\%\text{Acetyl}}{M(\text{Acetyl})}}{\frac{\%\text{cellulose } backbone}{M(AGU)}}$$

$$DS(Succinoyl) = \frac{\frac{\%Succinoyl}{M(Succinoyl)}}{\frac{\%\text{cellulose } backbone}{M(AGU)}}$$

$$M(MeO) = M(OCH_3) = 31.03Da$$
$$M(HPO) = M(OCH_2CH(OH)CH_3) = 75.09Da$$
$$M(\text{Acetyl}) = M(COCH_3) = 43.04Da$$
$$M(Succinoyl) = M(COC_2H_4COOH) = 101.08Da$$
$$M(AGU) = 162.14Da$$
$$M(OH) = 17.008Da$$
$$M(H) = 1.008Da$$

By convention, the weight percent is an average weight percentage based on the total weight of the cellulose repeat unit, including all substituents. The content of the methoxyl group is reported based on the mass of the methoxyl group (i.e., —$OCH_3$). The content of the hydroxyalkoxyl group is reported based on the mass of the hydroxyalkoxyl group (i.e., —O— alkylene-OH); such as hydroxypropoxyl (i.e., —O—$CH_2CH(CH_3)$—OH). The content of the aliphatic monovalent acyl groups is reported based on the mass of —C(O)—$R_1$ wherein $R_1$ is a monovalent aliphatic group, such as acetyl (—C(O)—$CH_3$). The content of the group of formula —C(O)—R—COOH is reported based on the mass of this group, such as the mass of succinoyl groups (i.e., —C(O)—$CH_2$—$CH_2$—COOH).

In one aspect of the present invention the esterified cellulose ethers have a viscosity a) of up to 1.80 mPa·s, preferably up to 1.70 mPa·s, more preferably up to 1.60, even more preferably up to 1.55 mPa·s, and most preferably up to 1.52 mPa·s, measured as a 2.0 wt % solution of the esterified cellulose ether in 0.43 wt.-% aqueous NaOH at 20° C. Generally the viscosity a) of the esterified cellulose ether is 1.20 mPa·s or more, typically 1.30 mPa·s or more, and more typically 1.40 mPa·s or more, measured as a 2.0 wt % solution of the esterified cellulose ether in 0.43 wt % aqueous NaOH at 20° C. The 2.0% by weight solution of the esterified cellulose ether is prepared as described in "Hypromellose Acetate Succinate, United States Pharmacopeia and National Formulary, NF 29, pp. 1548-1550", followed by an Ubbelohde viscosity measurement according to DIN 51562-1:1999-01 (January 1999). It has been found that the viscosity of the esterified cellulose ether in 0.43 wt % aqueous NaOH is very similar to the viscosity of the cellulose ether which is useful as a starting material for producing the esterified cellulose ether.

In another aspect of the present invention the esterified cellulose ethers have a viscosity b) of only up to 5.0 mPa·s, preferably only up to 4.0 mPa·s, and more preferably only up to 3.0 mPa·s, measured as a 10 wt % solution of the esterified cellulose ether in acetone at 20° C. The esterified cellulose ethers of the present invention typically has a viscosity of 1.20 mPa·s or more, more typically of 1.65 mPa·s or more, and most typically of 1.80 mPa·s or more, measured as a 10 wt % solution of the esterified cellulose ether in acetone at 20° C. The viscosity b) of the esterified cellulose ethers of this embodiment of the invention, measured as a 10 wt % solution in acetone, is much lower than the viscosity of known esterified cellulose ethers in acetone. This very low viscosity of the esterified cellulose ethers is highly advantageous when a liquid composition comprising the esterified cellulose ether is subjected to spray-drying, for example for preparing solid dispersions comprising an active ingredient and an esterified cellulose ether. The 10 wt % solution of the esterified cellulose ether in acetone can be prepared as in described in the Examples further below.

It has surprisingly been found that the esterified cellulose ethers of the invention typically have the above-described viscosity b) of only up to 5.0 mPa·s, measured as a 10 wt % solution of the esterified cellulose ether in acetone at 20° C., when the esterified cellulose ethers have the above-described viscosity a) of up to 1.80 mPa·s, measured as a 2.0 wt % solution of the esterified cellulose ether in 0.43 wt.-% aqueous NaOH at 20° C. Accordingly, in a preferred aspect of the present invention the esterified cellulose ethers have a combination of the viscosities a) and b) as described above. However, cellulose ethers which have the above-described viscosity a) of up to 1.80 mPa·s, measured as a 2.0 wt % solution of the esterified cellulose ether in 0.43 wt.-% aqueous NaOH at 20° C., but which have a somewhat higher viscosity, measured as a 10 wt % solution in acetone, e.g., a viscosity of up to 13 mPa·s, or up to 12 mPa·s, or up to 11 mPa·s, or up to 8.0 mPa·s, or up to 6.5 mPa·s, are also within the scope of the present invention. Moreover, cellulose ethers which have the above-described viscosity b) of only up to 5.0 mPa·s, measured as a 10 wt % solution of the esterified cellulose ether in acetone at 20° C., but which have a somewhat higher viscosity as a 2.0 wt % solution of the esterified cellulose ether in 0.43 wt.-% aqueous NaOH at 20° C., e.g., a viscosity of up to 2.33 mPa·s, or up to 2.25 mPa·s, or up to 2.10 mPa·s, or up to 1.95 mPa·s, measured as a 2.0 wt % solution of the esterified cellulose ether in 0.43 wt.-% aqueous NaOH at 20° C., are also within the scope of the present invention.

The average molecular weights of the esterified cellulose ethers of the present invention depends on various factors, such as the viscosity of the cellulose ether, measured as a 2.0 wt % solution in water at 20° C., which is used for preparing the esterified cellulose ethers of the present invention, and the weight ratios between the cellulose ether, diluent and catalyst that are used in the esterification reaction, as will be explained in more details below.

The esterified cellulose ethers generally have a weight average molecular weight $M_w$ of from 10,000 to 130,000 Dalton, or from 10,000 to 115,000 Dalton, or from 10,000 to 90,000 Dalton, or from 10,000 to 70,000 Dalton, or from 12,000 to 50,000 Dalton. The esterified cellulose ethers generally have a number average molecular weight $M_n$ of from 5000 to 19,000 Dalton or from 7000 to 18,000 or from 8,000 to 15,000 or from 9,000 to 13,000 Dalton and/or a z-average molecular weight, $M_z$, of from 20,000 to 900,000 Dalton or from 27,000 Dalton to 500,000 Dalton.

$M_w$, $M_n$ and $M_z$ are measured according to Journal of Pharmaceutical and Biomedical Analysis 56 (2011) 743 using a mixture of 40 parts by volume of acetonitrile and 60 parts by volume of aqueous buffer containing 50 mM $NaH_2PO_4$ and 0.1 M $NaNO_3$ as mobile phase. The mobile phase is adjusted to a pH of 8.0. The measurement of $M_w$, $M_n$ and $M_z$ is described in more details in the Examples.

The examples below describe how to prepare the esterified cellulose ethers of the present invention. Some aspects of the process for producing these esterified cellulose ethers will be described in more general terms below.

The esterified cellulose ethers of the present invention are typically produced from a cellulose ether which has a viscosity of from 1.20 to 1.80 mPa·s, preferably from 1.20 to 1.70 mPa·s, more preferably from 1.20 to 1.60 mPa·s, even more preferably from 1.20 to 1.55 mPa·s, and most preferably from 1.20 to 1.52 mPa·s, measured as a 2.0 wt % solution in water at 20° C. (+/−0.1° C.). The 2.0% by weight solution of a cellulose ether in water is prepared according to United States Pharmacopeia (USP 35, "Hypromellose", pages 3467-3469), followed by an Ubbelohde viscosity measurement according to DIN 51562-1:1999-01 (January 1999). A low viscosity cellulose ether used as a starting material allows for a good miscibility of the reaction mixture used for producing the esterified cellulose ethers resulting in a homogeneous reaction mixture. Preferably a cellulose ether is used which has the type of ether groups and the degree(s) of substitution of ether groups as described further above. The above-described cellulose ethers and their production are described in the international patent applications WO2009061821 and WO2009/061815.

The cellulose ether is reacted with (i) an aliphatic monocarboxylic acid anhydride or (ii) a dicarboxylic acid anhydride or (iii) a combination of an aliphatic monocarboxylic acid anhydride and a dicarboxylic acid anhydride. Preferred aliphatic monocarboxylic acid anhydrides are selected from the group consisting of acetic anhydride, butyric anhydride and propionic anhydride. Preferred dicarboxylic acid anhydrides are selected from the group consisting of succinic anhydride, maleic anhydride and phthalic anhydride. If a dicarboxylic acid anhydride and an aliphatic monocarboxylic acid anhydride are used in combination, the two anhydrides may be introduced into the reaction vessel at the same time or separately one after the other. The amount of each anhydride to be introduced into the reaction vessel is determined depending on the desired degree of esterification to be obtained in the final product, usually being 1 to 10 times the stoichiometric amounts of the desired molar degree of substitution of the anhydroglucose units by esterification. If an anhydride of a dicarboxylic acid is used, the molar ratio between the anhydride of a dicarboxylic acid and the anhydroglucose units of cellulose ether generally is 0.1/1 or more, and preferably 0.13/1 or more. The molar ratio between the anhydride of a dicarboxylic acid and the anhydroglucose units of cellulose ether generally is 1.5/1 or less, and preferably 1/1 or less. If an anhydride of a monocarboxylic acid is used, the molar ratio between the anhydride of an aliphatic monocarboxylic acid and the anhydroglucose units of the cellulose ether generally is 0.9/1 or more, and preferably 1.0/1 or more. The molar ratio between the anhydride of an aliphatic monocarboxylic acid and the anhydroglucose units of the cellulose ether generally is 8/1 or less, preferably 6/1 or less, and more preferably 4/1 or less. The molar number of anhydroglucose units of the cellulose ether utilized in the process of the present invention can be determined from the weight of the cellulose ether used as a starting material, by calculating the average molecular weight of the substituted anhydroglucose units from the DS(alkoxyl) and MS(hydroxyalkoxyl).

The esterification of the cellulose ether is preferably conducted in an aliphatic carboxylic acid as a reaction diluent, such as acetic acid, propionic acid, or butyric acid. The reaction diluent can comprise minor amounts of other solvents or diluents which are liquid at room temperature and do not react with the cellulose ether, such as aromatic or aliphatic solvents like benzene, toluene, 1,4-dioxane, or tetrahydrofurane; or halogenated $C_1$-$C_3$ derivatives, like dichloro methane or dichloro methyl ether, but the amount of the aliphatic carboxylic acid is preferably more than 50 percent, more preferably at least 75 percent, and even more preferably at least 90 percent, based on the total weight of the reaction diluent.

Most preferably the reaction diluent consists of an aliphatic carboxylic acid. Therefore, the esterification process is described below with reference to the use of an aliphatic carboxylic acid as reaction diluent although the process is not limited to it.

It has been found that the viscosity of an esterified cellulose ether, measured as a 10 wt % solution in acetone at 20° C., can be influenced by three major parameters of the esterification reaction: 1. the viscosity of the cellulose ether used as a starting material; 2. the molar ratio [aliphatic carboxylic acid/anhydroglucose units of cellulose ether]; and 3. the molar ratio [esterification catalyst/anhydroglucose units of cellulose ether]. Based on the general teaching herein and the more specific teaching in the Examples, the skilled artisan knows how to choose these three major parameters of the esterification reaction to arrive at the esterified cellulose ethers of the present invention.

Surprisingly, it has been found that an esterified cellulose ether with a significantly lower viscosity, measured as a 10 wt % solution in acetone, is obtained, when a cellulose ether is used as a starting material which has a viscosity of from 1.20 to 1.80 mPa·s, measured as a 2.0 wt % solution in water at 20° C., than when a cellulose ether of a viscosity of 3 mPa·s or more is used as disclosed in the prior art, while keeping the other reaction parameters constant. As illustrated by the Examples and Comparative Examples, the viscosity in acetone is much lower than could be expected in view of the slightly lower viscosity of the cellulose ether used as a starting material.

The appropriate molar ratio [aliphatic carboxylic acid/ anhydroglucose units of cellulose ether] depends on the viscosity of the cellulose ether used as a starting material. When the viscosity of the cellulose ether used as a starting material is only 1.2-1.8 mPa·s, measured as a 2.0 wt % solution in water at 20° C., the molar ratio [aliphatic carboxylic acid/anhydroglucose units of cellulose ether] can be as low as 1.5/1 or more, typically 1.7/1 or more, more typically 1.9/1 or more, while still preparing esterified cellulose ethers which have a viscosity of only up to 5 mPa·s, measured as a 10 wt % solution of the esterified cellulose ether in acetone at 20° C. If an esterified cellulose ether is obtained which has a too high viscosity, measured as a 10 wt % solution in acetone, the molar ratio [aliphatic carboxylic acid/anhydroglucose units of cellulose ether] should be increased in line with the present teaching.

The upper limit of the [aliphatic carboxylic acid/anhydroglucose units of cellulose ether] is not critical for obtaining the esterified cellulose ethers of the present invention. However, to achieve a reasonably high molecular weight, which is often desired, the molar ratio [aliphatic carboxylic acid/anhydroglucose units of cellulose ether] preferably is up to 11.5/1.0 or up to 10.0/1.0 or up to 8.0/1.0. The higher the molar ratio [aliphatic carboxylic acid/anhydroglucose units of cellulose ether] is, the lower is generally the weight average molecular weight of the esterified cellulose ethers, if the other reaction parameters are kept constant. The skilled artisans would expect that the viscosity of an esterified cellulose ether in acetone increases when its weight average molecular weight increases. However, it has very surprisingly been found that when cellulose ethers are used as a starting material which have a viscosity of only 1.20 to 2.0 mPa·s, more preferably from 1.20 to 1.80 mPa·s, and most preferably from 1.20 to 1.60 mPa·s, measured as a 2.0 wt % solution in water at 20° C., esterified cellulose ethers can be produced which have a high weight average molecular weight but still a low viscosity in acetone.

The esterification reaction is generally conducted in the presence of an esterification catalyst, preferably in the presence of an alkali metal carboxylate, such as sodium acetate or potassium acetate. The molar ratio [alkali metal carboxylate/anhydroglucose units of cellulose ether] is generally from [0.4/1.0] to [3.8/1.0], and preferably from [1.6/1.0] to [2.7/1.0]. The higher the molar ratio [alkali metal carboxylate/anhydroglucose units of cellulose ether] is, the higher is generally the weight average molecular weight of the esterified cellulose ethers, if the other reaction parameters are kept constant in the defined ranges. If an esterified cellulose ether is obtained which has a too high viscosity, measured as a 10 wt % solution in acetone, the molar ratio [alkali metal carboxylate/anhydroglucose units of cellulose ether] should be decreased or the molar ratio [aliphatic carboxylic acid/anhydroglucose units of cellulose ether] should be increased in line with the present teaching.

The reaction mixture is generally heated at 60° C. to 110° C., preferably at 70 to 100° C., for a period of time sufficient to complete the reaction, that is, typically from 2 to 25 hours, more typically from 2 to 8 hours. The reaction mixture should be thoroughly mixed to provide a homogeneous reaction mixture. After completion of the esterification reaction, the reaction product can be precipitated from the reaction mixture in a known manner, for example by contacting it with a large volume of water, such as described in U.S. Pat. No. 4,226,981, International Patent Application WO 2005/115330 or European Patent Application EP 0 219 426. In a preferred embodiment of the invention the reaction product is precipitated from the reaction mixture as described in U.S. Provisional Application 61/616,207, filed 27 Mar. 2012 or in its corresponding International Patent Application PCT/US13/030394, published as WO2013/148154.

Another aspect of the present invention is a composition comprising a liquid diluent and one or more of the above described esterified cellulose ethers. The term "liquid diluent" as used herein means a diluent that is liquid at 25° C. and atmospheric pressure. The diluent can be water or an organic liquid diluent or a mixture of water and an organic liquid diluent. Preferably the amount of the liquid diluent is sufficient to provide sufficient fluidity and processability to the composition for the desired usage, such as spray-drying or for coating purposes.

The term "organic liquid diluent" as used herein means an organic solvent or a mixture of two or more organic solvents. Preferred organic liquid diluents are polar organic solvents having one or more heteroatoms, such as oxygen, nitrogen or halogen like chlorine. More preferred organic liquid diluents are alcohols, for example multifunctional alcohols, such as glycerol, or preferably monofunctional alcohols, such as methanol, ethanol, isopropanol or n-propanol; ethers, such as tetrahydrofuran, ketones, such as acetone, methyl ethyl ketone, or methyl isobutyl ketone; acetates, such as ethyl acetate; halogenated hydrocarbons, such as methylene chloride; or nitriles, such as acetonitrile.

In one embodiment the composition of the present invention comprises as liquid diluent an organic diluent alone or mixed with a minor amount of water. In this embodiment the composition of the present invention preferably comprises more than 50, more preferably at least 65, and most preferably at least 75 weight percent of an organic liquid diluent and preferably less than 50, more preferably up to 35, and most preferably up to 25 weight percent of water, based on the total weight of the organic liquid diluent and water. This embodiment of the invention is of particularly useful if the present invention comprises an active ingredient of poor water solubility.

In another embodiment the composition of the present invention comprises as liquid diluent water alone or mixed with a minor amount of an organic liquid diluent as described above. In this embodiment the composition of the present invention preferably comprises at least 50, more preferably at least 65, and most preferably at least 75 weight percent of water and preferably up to 50, more preferably up to 35, and most preferably up to 25 weight percent of an organic liquid diluent, based on the total weight of the organic liquid diluent and water. This embodiment of the invention is particularly useful for providing coatings or capsules from aqueous compositions comprising the esterified cellulose ether of the present invention. When preparing an aqueous solution, it is preferred that at least a portion of the groups of formula —C(O)—R—COOA are in their salt form.

The composition of the present invention comprising a liquid diluent and one or more of the above described esterified cellulose ethers is useful as an excipient system for active ingredients and particularly useful as an intermediate for preparing an excipient system for active ingredients, such as fertilizers, herbicides or pesticides, or biologically active ingredients, such as vitamins, herbals and mineral supplements and drugs. Accordingly, the composition of the present invention preferably comprises one or more active ingredients, most preferably one or more drugs. The term "drug" is conventional, denoting a compound having beneficial prophylactic and/or therapeutic properties when administered to an animal, especially humans. Preferably, the drug is a "low-solubility drug", meaning that the drug has an aqueous solubility at physiologically relevant pH (e.g., pH 1-8) of about 0.5 mg/mL or less. The invention finds greater utility as the aqueous solubility of the drug decreases. Thus, compositions of the present invention are preferred for low-solubility drugs having an aqueous solubility of less than 0.1 mg/mL or less than 0.05 mg/mL or less than 0.02 mg/mL, or even less than 0.01 mg/mL where the aqueous solubility (mg/mL) is the minimum value observed in any physiologically relevant aqueous solution (e.g., those with pH values between 1 and 8) including USP simulated gastric and intestinal buffers. The active ingredient does not need to be a low-solubility active ingredient in order to benefit from this invention, although low-solubility active ingredients represent a preferred class for use with the invention. An active ingredient that exhibits appreciable aqueous solubility in the desired environment of use may have an aqueous solubility up to 1 to 2 mg/mL, or even as high as 20 to 40 mg/mL. Useful low-solubility drugs are listed in the International Patent Application WO 2005/115330, pages 17-22.

The liquid composition of the present invention preferably comprises from 1 to 40 percent, more preferably from 5 to 35 percent, even more preferably from 7 to 30 percent, and most preferably from 10 to 25 percent of at least one esterified cellulose ether as described above, from 40 to 99 percent, more preferably from 50 to 94.9 percent, even more preferably from 65 to 92.5 percent and most preferably from 70 to 89 percent of a liquid diluent described further above, and from 0 to 40 percent, more preferably from 0.1 to 40 percent, even more preferably from 0.5 to 25 percent, and most preferably from 1 to 15 percent of an active ingredient, based on the total weight of the composition. The low viscosity of the esterified cellulose ether, measured as a 10 wt % solution in acetone at 20° C., allows the incorporation of a high concentration of the esterified cellulose ether, i.e., a high ratio of esterified cellulose ether to liquid diluent, while still providing a liquid composition of reasonably low viscosity. This can be utilized in two ways to produce solid dispersions of an active ingredient in an esterified cellulose ether: 1. Either the ratio of esterified cellulose ether/active ingredient is kept the same as in known, more dilute compositions. In this case a higher concentration of the esterified cellulose ether also leads to a higher concentration of the active ingredient in the liquid composition, and, accordingly to an increased throughput of the active ingredient in the production of solid dispersions while maintaining the same stability of the active ingredient. 2. Alternatively, only the concentration of the esterified cellulose ether in the liquid composition is increased, but not the concentration of the active ingredient. This leads to a higher ratio of esterified cellulose ether/active ingredient, which leads to an improved stabilization of the active ingredient in the matrix of the esterified cellulose ether upon removal of the liquid diluent without decreasing the throughput of the active ingredient. This means that formulators can operate at a higher content of the esterified cellulose ether in the liquid formulation—without the need to reduce the content of the active ingredient—in order to achieve enhanced stabilization of the amorphous state of an active ingredient in a solid dosage form. The esterified cellulose ethers of the present invention allow a high loading of the active ingredient in the liquid composition while still achieving a reasonably high throughput in preparing a solid dispersion. The production of semi-ordered instead of amorphous dispersions to achieve a higher active ingredient throughput as proposed in WO2004/014342, page 13, last paragraph, is not necessary.

In one aspect of the invention the composition comprising at least one esterified cellulose ether as described above, one or more active ingredients and optionally one or more adjuvants can be used in liquid form, for example in the form of a suspension, a slurry, a sprayable composition, or a syrup. The liquid composition is useful, e.g., for oral, ocular, topical, rectal or nasal applications. The liquid diluent should generally be pharmaceutically acceptable, such as ethanol or glycerol, optionally mixed with water as described above. The low viscosity of the esterified cellulose ether in acetone or another organic solvent significantly improves the handling of the liquid composition, such as its ability of being poured or pumped.

In another aspect of the invention the liquid composition of the present invention is used for producing a solid dispersion comprising at least one active ingredient, such as a drug described further above, at least one esterified cellulose ether as described above and optionally one or more adjuvants. The solid dispersion is produced by removing the liquid diluent from the composition. The low viscosity of the esterified cellulose ether in acetone or another organic solvent allows the incorporation of a high concentration of the esterified cellulose ether, and accordingly a high concentration of a drug, into the composition while still maintaining a reasonably low viscosity of the liquid composition. This is highly advantageous for achieving a high throughput when the liquid composition is used for coating purposes or when the comprising the esterified cellulose ether is subjected to spray-drying, for example for preparing solid dispersions comprising an active ingredient and an esterified cellulose ether. Moreover, liquid formulations using a high ratio of esterified cellulose ether to active ingredient, as described above, can be formulated with spray drying. A high ratio of esterified cellulose ether to active ingredient is desired in maintaining supersaturation of poorly soluble active ingredients and for increasing its bioavailability.

One method of removing the liquid diluent from the liquid composition is by casting the liquid composition into a film or a capsule or by applying the liquid composition onto a solid carrier that in turn may comprise an active ingredient. The use of the liquid composition of the present invention for coating purposes is a preferred aspect of the present invention.

A preferred method of producing a solid dispersion is by spray-drying. The term "spray-drying" refers to processes involving breaking up liquid mixtures into small droplets (atomization) and rapidly removing solvent from the mixture in a spray-drying apparatus where there is a strong driving force for evaporation of solvent from the droplets. Spray-drying processes and spray-drying equipment are described generally in Perry's Chemical Engineers' Handbook, pages 20-54 to 20-57 (Sixth Edition 1984). More details on spray-drying processes and equipment are reviewed by Marshall, "Atomization and Spray-Drying," 50 Chem. Eng. Prog. Monogr. Series 2 (1954), and Masters, Spray Drying Handbook (Fourth Edition 1985). A useful spray-drying process is described in the International Patent Application WO 2005/115330, page 34, line 7-page 35, line 25. Alternatively, the solid dispersion of the present invention may be prepared by i) blending a) at least one esterified cellulose ether defined above, b) one or more active ingredients and c) one or more optional additives, and ii) subjecting the blend to extrusion. The term "extrusion" as used herein includes processes known as injection molding, melt casting and compression molding. Techniques for extruding, preferably melt-extruding compositions comprising an active ingredient such as a drug are known and described by Joerg Breitenbach, Melt extrusion: from process to drug delivery technology, *European Journal of Pharmaceutics and Biopharmaceutics* 54 (2002) 107-117 or in European Patent Application EP 0 872 233. The solid dispersion of the present invention preferably comprises from 20 to 99.9 percent, more preferably from 30 to 98 percent, and most preferably from 60 to 95 percent of an esterified cellulose ether a) as described above, and preferably from 0.1 to 80 percent, more preferably from 2 to 70 percent, and most preferably from 5 to 40 percent of an active ingredient b), based on the total weight of the esterified cellulose ether a) and the active ingredient b). The combined amount of the esterified cellulose ether a) and the active ingredient b) is preferably at least 70 percent, more preferably at least 80 percent, and most preferably at least 90 percent, based on the total weight of the solid dispersion. The remaining amount, if any, consists of one or more of the adjuvants c) as described below. The solid dispersion can comprise one or more of the esterified cellulose ethers a), one or more of the active ingredients b), and optionally one or more of the adjuvants c), however their total amount is generally within the above-mentioned ranges.

Once the solid dispersion comprising at least one active ingredient in at least one esterified cellulose ether has been formed, several processing operations can be used to facilitate incorporation of the dispersion into a dosage form. These processing operations include drying, granulation, and milling. The inclusion of optional adjuvants in the solid dispersion may be useful in order to formulate the composition into dosage forms. The solid dispersion of the present invention may be in various forms, such as in the form of strands, pellets, granules, pills, tablets, caplets, microparticles, fillings of capsules or injection molded capsules or in the form of a powder, film, paste, cream, suspension or slurry.

The amount of the active ingredient in the dosage form is generally is at least 0.1 percent, preferably at least 1 percent, more preferably at least 3 percent, most preferably at least 5 percent and generally up to 70 percent, preferably up to 50 percent, more preferably up to 30 percent, most preferably up to 25 percent, based on the total weight of the dosage form.

In another aspect of the invention the composition of the present invention comprising a liquid diluent and one or more of the above described esterified cellulose ethers may be used for coating dosage forms, such as tablets, granules, pellets, caplets, lozenges, suppositories, pessaries or implantable dosage forms, to form a coated composition. If the composition of the present invention comprises an active ingredient, such as a drug, drug layering can be achieved, i.e., the dosage form and the coating may comprise different active ingredients for different end-uses and/or having different release kinetics.

In yet another aspect of the invention the composition of the present invention comprising a liquid diluent and one or more of the above described esterified cellulose ethers may be used for the manufacture of capsules in a process which comprises the step of contacting the liquid composition with dipping pins.

The liquid composition and the solid dispersion of the present invention may further comprise optional additives, such as coloring agents, pigments, opacifiers, flavor and taste improvers, antioxidants, and any combination thereof. Optional additives are preferably pharmaceutically acceptable. Useful amounts and types of one or more optional adjuvants are generally known in the art and depend on the intended end-use of the liquid composition or the solid dispersion of the present invention.

Some embodiments of the invention will now be described in detail in the following Examples.

EXAMPLES

Unless otherwise mentioned, all parts and percentages are by weight. In the Examples the following test procedures are used.

Viscosity of Hydroxypropyl Methyl Cellulose (HPMC) Samples

The viscosity of the HPMC samples was measured as a 2.0% by weight solution in water at 20° C.±0.1° C. The 2.0% by weight HPMC solution in water was prepared according to United States Pharmacopeia (USP 35, "Hypromellose", pages 3467-3469), followed by an Ubbelohde viscosity measurement according to DIN 51562-1:1999-01 (January 1999).

Viscosity of Hydroxypropyl Methyl Cellulose Acetate Succinate (HPMCAS)

The 2.0% by weight solution of the HPMCAS in 0.43 wt % aqueous NaOH was prepared as described in "Hypromellose Acetate Succinate, United States Pharmacopia and National Formulary, NF 29, pp. 1548-1550", followed by an Ubbelohde viscosity measurement at 20° C. according to DIN 51562-1:1999-01 (January 1999).

The 10 wt % solution of the esterified cellulose ether in acetone was prepared by first determining the loss on drying of the HPMCAS according "Hypromellose Acetate Succinate, United States Pharmacopia and National Formulary, NF 29, pp. 1548-1550". Subsequently 10.00 g HPMCAS, based on its dry weight, was mixed with 100 g of acetone under vigorous stirring at room temperature. The mixture was rolled on a roller mixer for about 24 hours. The solution was centrifuged at 2000 rpm for 3 minutes using a Megafuge 1.0 centrifuge, commercially available from Heraeus Holding GmbH, Germany, followed by an Ubbelohde viscosity measurement at 20° C. according to DIN 51562-1:1999-01 (January 1999).

Content of Ether and Ester Groups of HPMCAS

The content of ether groups in the esterified cellulose ether was determined in the same manner as described for "Hypromellose", United States Pharmacopeia and National Formulary, USP 35, pp 3467-3469.

The ester substitution with acetyl groups ($-CO-CH_3$) and the ester substitution with succinoyl groups ($-CO-CH_2-CH_2-COOH$) were determined according to Hypromellose Acetate Succinate, United States Pharmacopia and National Formulary, NF 29, pp. 1548-1550". Reported values for ester substitution were corrected for volatiles (determined as described in section "loss on drying" in the above HPMCAS monograph).

Determination of $M_w$, $M_n$ and $M_z$ of HPMCAS $M_w$, $M_n$ and $M_z$ were measured according to Journal of Pharmaceutical and Biomedical Analysis 56 (2011) 743 unless stated otherwise. The mobile phase was a mixture of 40 parts by volume of acetonitrile and 60 parts by volume of aqueous buffer containing 50 mM $NaH_2PO_4$ and 0.1 M $NaNO_3$. The mobile phase was adjusted to a pH of 8.0. Solutions of the cellulose ether esters were filtered into a HPLC vial through a syringe filter of 0.45 μm pore size.

More specifically, the utilized Chemicals and solvents were:

Polyethylene oxide standard materials (abbreviated as PEOX 20 K and PEOX 30 K) were purchased from Agilent Technologies, Inc. Palo Alto, Calif., catalog number PL2083-1005 and PL2083-2005.

Acetonitrile (HPLC grade ≥99.9%, CHROMASOL plus), catalog number 34998, sodium hydroxide (semiconductor grade, 99.99%, trace metal base), catalog number 306576, water (HPLC grade, CHROMASOLV Plus) catalog number 34877 and sodium nitrate (99,995%, trace metal base) catalog number 229938 were purchased from Sigma-Aldrich, Switzerland.

Sodium dihydrogen phosphate (≥99.999% TraceSelect) catalog number 71492 was purchased from FLUKA, Switzerland.

The normalization solution of PEOX20 K at 5 mg/mL, the standard solution of PEOX30 K at 2 mg/mL, and the sample solution of HPMCAS at 2 mg/mL were prepared by adding a weighed amount of polymer into a vial and dissolving it with a measured volume of mobile phase. All solutions were allowed to dissolve at room temperature in the capped vial for 24 h with stirring using a PTFE-coated magnetic stirring bar.

The normalization solution (PEOX 20 k, single preparation, N) and the standard solution (PEOX30 K, double preparation, S1 and S2) were filtered into a HPLC vial through a syringe filter of 0.02 μm pore size and 25 mm diameter (Whatman Anatop 25, catalog number 6809-2002), Whatman.

The test sample solution (HPMCAS, prepared in duplicate, T1, T2) and a laboratory standard (HPMCAS, single preparation, LS) were filtered into a HPLC vial through a syringe filter of 0.45 μm pore size (Nylon, e.g. Acrodisc 13 mm VWR catalog number 514-4010).

Chromatographic condition and run sequence were conducted as described by Chen, R. et al.; Journal of Pharmaceutical and Biomedical Analysis 56 (2011) 743-748). The SEC-MALLS instrument set-up included a HP1100 HPLC system from Agilent Technologies, Inc. Palo Alto, Calif.; a DAWN Heleos II 18 angle laser light scattering detector and a OPTILAB rex refractive index detector, both from Wyatt Technologies, Inc. Santa Barbara, Calif. The analytical size exclusion column (TSK-GEL® GMPWXL, 300×7 8 mm) was purchased from Tosoh Bioscience. Both the OPTILAB and the DAWN were operated at 35° C. The analytical SEC column was operated at room temperature (24±5° C.). The mobile phase was a mixture of 40 volume parts of acetonitrile and 60 volume parts of aqueous buffer containing 50 mM NaH2PO4 and 0.1 M NaNO3 prepared as follows:

Aqueous buffer: 7.20 g of sodium dihydrogen phosphate and 10.2 g of sodium nitrate were added to 1.2 L purified water in a clean 2 L glass bottle under stirring until dissolution.

Mobile phase: 800 mL of acetonitrile were added to 1.2 L of the aqueous buffer prepared above, and stirred until a good mixture was achieved and the temperature equilibrated to ambient temperature.

The mobile phase was pH adjusted to 8.0 with 10M NaOH and filtered through a 0.2 m nylon membrane filter. The flow rate was 0.5 mL/min with in-line degassing. The injection volume was 100 μL and the analysis time was 35 min.

The MALLS data were collected and processed by Wyatt ASTRA software (version 5.3.4.20) using dn/dc value (refractive index increment) of 0.120 mL/g for HPMCAS. The light scattering signals of detector Nos. 1-4, 17, and 18) were not used in the molecular weight calculation. A representative chromatographic run sequence is given below: B, N, LS, S1 (5×), S2, T1 (2×), T2 (2×), T3 (2×), T4 (2×), S2, T5(2×), etc., S2, LS, W, where, B represents blank injection of mobile phase, N1 represents normalization solution; LS represents a laboratory standard HPMCAS; S1 and S2 represent standard solutions one and two, respectively; T1, T2, T3, T4, and T5 represent test sample solutions and W represents water injection. (2×) and (5×) denote the number of injections of the same solution.

Both the OPTILAB and the DAWN were calibrated periodically according to the manufacturer's recommended procedures and frequency. A 100 μL injection of a 5 mg/mL polyethylene oxide standard (PEOX20 K) was employed for normalizing all angle light scattering detectors relative to 90° detector for each run sequence.

Use of this mono-dispersed polymer standard also enabled the volume delay between the OPTILAB and the DAWN to be determined, permitting proper alignment of the light scattering signals to the refractive index signal. This is necessary for the calculation of the weight-averaged molecular weight (Mw) for each data slice.

Production of Hydroxypropyl Methyl Cellulose Acetate Succinate (HPMCAS) of Examples 1-6

Glacial acetic acid, acetic anhydride, a hydroxypropyl methylcellulose (HPMC), succinic anhydride and sodium acetate (water free) were introduced in the amounts listed in Table 1 below into a reaction vessel under thorough stirring to produce a homogeneous reaction mixture. The HPMC had a methoxyl and hydroxypropoxyl substitution and a viscosity, measured as a 2% solution in water at 20° C., as listed in Table 2 below.

The mixture was heated at 85° C. with agitation for 3 or 3.5 hours, as listed in Table 1 below, to effect esterification. x L of water was added to the reactor under stirring to precipitate the HPMCAS. The precipitated product was removed from the reactor and washed with y L of water by applying high shear mixing using an Ultra-Turrax stirrer 550-G45 running at 5200 rpm. The washing was conducted in several portions with intermediate filtration steps to obtain HPMCAS of very high purity. The HPMCAS products should be washed and filtrated until their viscosity is substantially constant (10 wt. % in acetone). The numbers of L of water x and y are listed in Table 1 below. After the last filtration step the product was dried at 50° C. overnight.

Production of HPMCAS of Comparative Examples A and B

The production of HPMCAS according to Comparative Examples A and B was carried out as in Examples 1 to 6, except that a HPMC of a higher viscosity was used, as listed in Table 2 below. The HPMC is commercially available from The Dow Chemical Company as Methocel E3 LV Premium cellulose ether.

Production of HPMCAS of Comparative Example C

The production of HPMCAS according to Comparative Example C was carried out as in Examples 1 to 6, except that the type of HPMC and the weight ratios of glacial acetic acid, acetic anhydride, HPMC, succinic anhydride and sodium acetate (water free) were used as disclosed in Example 2 of European Patent Application EP 0219 426 A2. The used amounts are listed in Table 1 below.

The HPMC used in Comparative Example C had a viscosity of 3.1 mPa·s, measured as a 2% solution in water at 20° C. The HPMC contained 9.3% by weight of hydroxypropoxyl groups and about 28.2% by weight of methoxyl groups. This HPMC is commercially available from The Dow Chemical Company as Methocel E3 LV Premium cellulose ether.

The mixture was heated at 85° C. with agitation for 3.5 hours to effect esterification. x L of water was added to the reactor under stirring to precipitate the HPMCAS. The precipitated product was removed from the reactor and washed with y L of water by applying high shear mixing using an Ultra-Turrax stirrer S50-G45 running at 5200 rpm. The numbers of water x and y are listed in Table 1 below. The product was isolated by filtration and dried at 55° C. for 12 h.

The obtained ester substitutions % acetyl and % succinoyl in Comparative Example C was significantly different from those disclosed in Example 2 of European Patent Application EP 0219 426 A2. Therefore, Comparative Example C was repeated. The obtained ester substitutions % acetyl and % succinoyl in the repeated Example C were substantially the same as in the first Comparative Example C. The results in Table 2 show the average of the two runs of Comparative Example C.

Production of HPMCAS of Comparative Examples D and E

The production of HPMCAS according to Comparative Examples D and E was carried out as in Examples 1 to 6, except that the weight ratios of glacial acetic acid, acetic anhydride, HPMC, succinic anhydride and sodium acetate (water free) were used as disclosed International Patent Application WO 2005/115330, pages 51 and 52, polymers 1 and 3. The product was obtained, separated and washed as described in International Patent Application WO 2005/115330. The reaction mixture was quenched into 2.4 L of water, precipitating the polymer. An additional 1 L of water was used to complete the precipitation for example D only. The polymer was then isolated and washed with 3×300 mL of water. Then the polymer was dissolved in 600 mL of acetone and again precipitated in 2.4 L of water. To complete precipitation another 1 L of water was added.

Comparative Examples F to H

As disclosed in International Patent Application WO 2011/159626 on pages 1 and 2, HPMCAS is currently commercially available from Shin-Etsu Chemical Co., Ltd. (Tokyo, Japan), known by the trade name "AQOAT". Shin-Etsu manufactures three grades of AQOAT polymers that have different combinations of substituent levels to provide enteric protection at various pH levels, AS-L, AS-M, and AS-H, typically followed by the designation "F" for fine or "G", such as AS-LF or AS-LG. Their sales specifications are listed below.

Properties of AQOAT polymers as listed in WO 2011/159626

| | Designation of analyzed commercial samples: Comparative Example | | |
|---|---|---|---|
| | F | G | H |
| | Substituent content Published Composition of AQOAT polymers (wt %) | | |
| | L-Grade | M-Grade | H-Grade |
| Methoxyl | 20.0-24.0 | 21-0-25.0 | 22.0-26.0 |
| Hydroxypropoxyl | 5.0-9.0 | 5.0-9.0 | 6.0-10.0 |
| Acetyl | 5.0-9.0 | 7.0-11.0 | 10.0-14.0 |
| Succinoyl | 14.0-18.0 | 10-14 | 4.0-8.0 |

Samples of the commercially available materials were analyzed as described further above.

The properties of the HPMCAS produced according to Examples 1-6 and comparative Examples A-E and the properties of the commercially available Comparative Examples F to H are listed in Table 2 below.

In Table 2 below the abbreviations have the following meanings:

$DS_M$=DS(methoxyl): degree of substitution with methoxyl groups;
$MS_{HP}$=MS(hydroxypropoxyl): molar subst. with hydroxypropoxyl groups;
$DOS_{Ac}$: degree of substitution of acetyl groups;
$DOS_s$: degree of substitution of succinoyl groups.

TABLE 1

| Table 1 (Comp.) Example | HPMC* | | HPMC, 2% viscosity in water (mPa·s) | acetic acid | | Succinic anhydride | | Acetic anhydride | | Sodium acetate | | Heating at 85° C. hours | x L of water | y L of water |
|---|---|---|---|---|---|---|---|---|---|---|---|---|---|---|
| | g | Mol | | g | mol/mol HPMC | g | mol/mol HPMC | g | mol/mol HPMC | g | mol/mol HPMC | | | |
| 1 | 50.0 | 0.25 | 1.5 | 113.3 | 7.6 | 14.0 | 0.57 | 65.0 | 2.69 | 50.0 | 2.47 | 3.5 | 0.6 | 12 |
| 2 | 50.0 | 0.25 | 1.5 | 100.0 | 6.7 | 14.0 | 0.57 | 65.0 | 2.69 | 50.0 | 2.47 | 3.5 | 0.6 | 10 |
| 3 | 40.0 | 0.20 | 1.5 | 74.6 | 6.3 | 11.2 | 0.57 | 52.0 | 2.69 | 40.0 | 2.47 | 3.5 | 0.6 | 10 |
| 4 | 215 | 1.06 | 1.5 | 231 | 3.6 | 35.5 | 0.33 | 130.2 | 1.25 | 86.94 | 1.00 | 3.5 | 3.06 | 11 |
| 5 | 60 | 0.3 | 1.39 | 35 | 2.0 | 10.13 | 0.34 | 37.2 | 1.28 | 17.4 | 0.72 | 3.5 | 0.8 | 27 |
| 6 | 60 | 0.3 | 1.39 | 30 | 1.7 | 10.13 | 0.34 | 37.2 | 1.28 | 17.4 | 0.72 | 3.5 | 0.8 | 29 |
| A | 35.0 | 0.17 | 2.25 | 38.5 | 3.7 | 5.91 | 0.34 | 21.7 | 1.28 | 14.48 | 1.02 | 3.5 | 0.47 | 27 |
| B | 195.0 | 0.97 | 3.1 | 442.0 | 7.6 | 54.6 | 0.57 | 253.5 | 2.69 | 195.0 | 2.47 | 3.5 | 1.8 | 35 |
| C | 200 | 0.96 | 3.1 | 600 | 10.2 | 50 | 0.51 | 76 | 0.78 | 160 | 1.97 | 3.5 | 2.4 | 11 |
| D | 80 | 0.40 | 3.1 | 420 | 17.7 | 18.9 | 0.48 | 640.2 | 16.53 | 40.43 | 1.25 | 21.75 | See Comp. Examples D and E above | |
| E | 80 | 0.40 | 3.1 | 420 | 17.7 | 13.2 | 0.33 | 432.8 | 11.17 | 40.43 | 1.25 | 21.75 | | |

*calculated on the dried basis

TABLE 2

| Table 2 (Comp.) Example | Molecular weight (kDA) | | | 10% visc. in acetone (mPa·s) | 2% visc. in NaOH (mPa·s) | Ether Substitution | | Ester substitution | | Ether Substitution | | Ester substitution | |
|---|---|---|---|---|---|---|---|---|---|---|---|---|---|
| | Mn | Mw | Mz | | | Methoxyl (%) | Hydroxy-Propoxyl, % | Acetyl (%) | Succinoyl (%) | $DS_M$ | $MS_{HP}$ | $DOS_{Ac}$ | $DOS_s$ |
| 1 | 9 | 14 | 28 | 1.79 | 1.46 | 23.3 | 7.0 | 9.6 | 12.9 | 1.97 | 0.24 | 0.58 | 0.33 |
| 2 | 9 | 15 | 29 | 2.05 | 1.43 | 23.4 | 7.0 | 9.7 | 13.1 | 1.99 | 0.25 | 0.59 | 0.34 |
| 3 | 9 | 14 | 28 | 1.86 | 1.44 | 23.3 | 7.0 | 9.8 | 13.2 | 1.98 | 0.25 | 0.60 | 0.34 |
| 4 | 11 | 24 | 75 | 1.97 | 1.60 | 23.1 | 7.8 | 10.0 | 11.3 | 1.93 | 0.27 | 0.60 | 0.29 |
| 5 | 10 | 41 | 185 | 1.81 | 1.49 | 22.7 | 7.7 | 9.8 | 12.3 | 1.91 | 0.27 | 0.59 | 0.32 |

TABLE 2-continued

| Table 2 (Comp.) Example | Molecular weight (kDA) | | | 10% visc. in acetone (mPa·s) | 2% visc. in NaOH (mPa·s) | Ether Substitution | | Ester substitution | | Ether Substitution | | Ester substitution | |
|---|---|---|---|---|---|---|---|---|---|---|---|---|---|
| | Mn | Mw | Mz | | | Methoxyl (%) | Hydroxy-Propoxyl, % | Acetyl (%) | Succinoyl (%) | $DS_M$ | $MS_{HP}$ | $DOS_{Ac}$ | $DOS_s$ |
| 6 | 12 | 112 | 863 | 2.41 | 1.49 | 22.7 | 7.7 | 10.2 | 11.6 | 1.90 | 0.27 | 0.62 | 0.30 |
| A | 20 | 80 | 403 | 15.1 | 2.18 | 24.4 | 7.2 | 7.9 | 10.9 | 1.96 | 0.24 | 0.46 | 0.27 |
| B | 36 | 139 | 1540 | 37.4 | 2.61 | 22.7 | 7.5 | 11.0 | 12.1 | 1.94 | 0.26 | 0.68 | 0.32 |
| C | 26 | 65 | 329 | 16.6 | 2.89 | 22.9 | 7.3 | 5.7 | 16.0 | 1.91 | 0.25 | 0.34 | 0.41 |
| D | 23 | 51 | 462 | 12.8 | 2.86 | 22.3 | 7.4 | 11.7 | 11.7 | 1.90 | 0.26 | 0.72 | 0.31 |
| E | 22 | 54 | 1158 | 13.5 | 2.86 | 22.6 | 7.1 | 12.6 | 9.1 | 1.87 | 0.24 | 0.75 | 0.23 |
| F | 33 | 153 | 889 | 27.7 | 3.0 | 22.5 | 7.0 | 8.1 | 14.7 | 1.90 | 0.24 | 0.49 | 0.38 |
| G | 27 | 114 | 654 | 22.9 | 2.94 | 23.1 | 7.3 | 9.3 | 10.6 | 1.88 | 0.24 | 0.54 | 0.26 |
| H | 29 | 137 | 821 | 29.8 | 2.89 | 23.6 | 7.2 | 11.6 | 7.9 | 1.90 | 0.24 | 0.67 | 0.19 |

Examples 1-6 illustrate that the esterified cellulose ethers of the present invention have a very low viscosity, measured as a 10 wt % solution in acetone at 20° C. Solutions of these esterified cellulose ethers in organic solvents, such as acetone, can be very efficiently processed. For example, a very fast throughput in spray-drying and coating operations at high concentrations of the esterified cellulose ether can be achieved.

Moreover, it has surprisingly been found that esterified cellulose ethers of the present invention can be provided which have a very low viscosity, measured as a 10 wt % solution in acetone, even if the esterified cellulose ethers of the present invention have a relatively high molecular weight. Achieving a very low viscosity in acetone irrespective of the weight average molecular weight provides great advantages. The molecular weight of the esterified cellulose ether can be adapted to the specific needs of an active ingredient, such as a drug, while the efficient processing of the esterified cellulose ethers in organic solvents, such as acetone, is not affected.

As illustrated by Comparative Examples A to H, an increased weight average molecular weight usually leads to an increased viscosity, measured as a 10 wt % solution in acetone. It is known to the skilled artisan that these properties are also somewhat influenced by the % acetyl and % succinoyl.

The weight ratios of glacial acetic acid, acetic anhydride, HPMC, succinic anhydride and sodium acetate (water free) in Comparative Example A correspond to those in Example 4. The weight ratios in Comparative Example B correspond to those in Example 1. The comparison between Example 1 and Comparative Example B and the comparison between Example 4 and Comparative Example A illustrate that a much lower viscosity, measured as a 10 wt % solution in acetone, is obtained, even if the viscosity of the HPMC used as a starting material is not much lower and even if the molar ratios of the reactants are kept constant.

Impact of Cellulose Ethers on the Aqueous Solubility of a Poorly Soluble Drug

The ability of the esterified cellulose ethers of Example 3 and of Comparative Examples F-G to maintain drug concentrations in an aqueous solution at supersaturation levels was tested with the poorly water soluble drugs Griseofulvin and Phenytoin. Griseofulvin has a water solubility of 8.54 mg/l, a log P of 2.2, a Tm of 220° C., a Tg of 85° C., and, accordingly a Tm/Tg=493° K/358° K=1.39. [Feng, Tao et. al.; J. Pharm. Sci.; Vol. 97, No. 8, 2008, pg 3207-3221 and W. Curatolo, Pharmaceutical Research, Vol. 26, No. 6, June 2009, pg 1422]. Griseofulvin belongs to group 2 on the map Tm/Tg ratio versus log P (FIG. 14 on page 1018 in MOLECULAR PHARMACEUTICS VOL. 5, NO. 6).

Phenytoin has a water solubility of 32 mg/1, a log P of 2.47, a Tm of 295° C., a Tg of 71° C. and, accordingly a Tm/Tg=568° K/344° K=1.65 [Friesen et al., MOLECULAR PHARMACEUTICS VOL. 5, NO. 6, 1003-1019 and W. Curatolo, Pharmaceutical Research, Vol. 26, No. 6, June 2009, pg 1422]. Phenytoin belongs to group 3 on the map Tm/Tg ratio versus log P (FIG. 14 on page 1018 in MOLECULAR PHARMACEUTICS VOL. 5, NO. 6, 2008).

Solutions of an esterified cellulose ether listed in Table 3 below (950 µl, 3.16 mg/L) in phosphate buffered saline (82 mM sodium chloride, 20 mM sodium phosphate dibasic, 47 mM potassium phosphate monobasic, 0.5 wt % simulated intestinal fluid powder, pH 6.5) at 37° C. were robotically delivered into designated 1 mL vials arranged in an aluminum 96 (8×12) well block heated to 37° C. using a Tecan 150 liquid handler. Organic drug solutions at 37° C. were dispensed onto the phosphate buffered saline aqueous solution comprising an esterified cellulose ether listed in Table 3 below. The organic drug solution was a) 20 g/L griseofulvin in dimethylformamide, 50 µL, final maximum drug concentration of 1000 mg/L, or b) 20 g/L phenytoin in dimethylformamide, 50 µL, final maximum drug concentration of 1000 mg/L. The robot aspirated and dispensed liquid in a set sequence for each vial for about 30 s to mix. After 180 minutes the vials were centrifuged 1 min at about 3200×g (g=gravitational force on earth). An aliquot (30 µl) was transferred to methanol (150 µl) in a 96-well plate, sealed, briefly gently agitated to mix, and then the drug concentration was analyzed by HPLC.

In a Control Run the experiment was carried out as described above with a phosphate buffered saline aqueous solution which did not contain any amount of cellulose ether.

In Table 3 below the concentrations (averages of four experimental replicates) of Griseofulvin and Phenytoin are listed that have not precipitated upon centrifugation after 180 minutes but that remain dissolved in the phosphate buffered saline aqueous solution. The error margins of the concentrations are about 10%.

The results in Table 3 below illustrate that the esterified cellulose ethers of the present invention are able to maintain the concentration of poorly water-soluble drugs in an aqueous solution at supersaturation levels. The data in Table 3 further illustrates that this ability is comparable to this ability of comparable known esterified cellulose ethers, even when the esterified cellulose ethers of the present invention have a significantly lower viscosity, measured as a 10 wt. % solution in acetone, and a significantly lower weight average molecular weight. This finding is highly surprising and illustrates the great advantages of the esterified cellulose ethers of the present invention as excipients for active ingredients of low water-solubility. The esterified cellulose ethers of the present invention combine easy processability in solutions, particularly in organic solutions, and high ability maintain to the concentration of poorly water-soluble drugs in an aqueous solution at supersaturation levels.

TABLE 3

| (Comp.) Example | Methoxyl (%) | Hydroxy-Propoxyl (%) | Acetyl (%) | Succinoyl (%) | 2% viscosity in NaOH [mPa·s] | Mn [kDa] | Mw [kDa] | Mz [kDa] | 10% viscosity in acetone [mPa·s] | Griseofulvin concentration [mg/L] at 180 min. | Phenytoin concentration [mg/L] at 180 min. |
|---|---|---|---|---|---|---|---|---|---|---|---|
| 3 | 23.3 | 7.0 | 9.8 | 13.2 | 1.44 | 9 | 14 | 28 | 1.86 | 810 | 350 |
| F | 22.5 | 7.0 | 8.1 | 14.7 | 3.00 | 33 | 153 | 889 | 27.7 | 360 | 230 |
| G | 23.1 | 7.3 | 9.3 | 10.6 | 2.94 | 27 | 114 | 654 | 26.5 | 800 | 270 |
| Control | — | — | — | — | — | — | — | — | — | 128 | 65 |

The invention claimed is:

1. An esterified cellulose ether comprising (i) aliphatic monovalent acyl groups or (ii) groups of the formula —C(O)—R—COOA, wherein R is a divalent aliphatic or aromatic hydrocarbon group and A is hydrogen or a cation, or (iii) a combination of aliphatic monovalent acyl groups and groups of the formula —C(O)—R—COOA, wherein the esterified cellulose ether has a) a viscosity of from 1.2 to 2.10 mPa·s, measured as a 2.0 wt. % solution of the esterified cellulose ether in 0.43 wt. % aqueous NaOH at 20° C., and b) a viscosity of up to 5 mPa·s, measured as a 10 wt. % solution of the esterified cellulose ether in acetone at 20° C. and wherein the esterified cellulose ether is produced by esterifying a cellulose ether having a viscosity of from 1.2 to 1.8 mPa·s, measured as a 2 wt. % solution in water at 20° C. with (i) an aliphatic monocarboxylic acid anhydride or (ii) a dicarboxylic acid anhydride or (iii) a combination of an aliphatic monocarboxylic acid anhydride and a dicarboxylic acid anhydride.

2. The esterified cellulose ether of claim 1 having a) a viscosity of from 1.2 to 1.8 mPa·s, measured as a 2.0 wt % solution of the esterified cellulose ether in 0.43 wt % aqueous NaOH at 20° C., and b) a viscosity of up to 5 mPa·s, measured as a 10 wt % solution of the esterified cellulose ether in acetone at 20° C.

3. The esterified cellulose ether of claim 1 having a viscosity of up to 3 mPa·s, measured as a 10 wt % solution of the esterified cellulose ether in acetone at 20° C.

4. The esterified cellulose ether of claim 1 having a viscosity of from 1.20 to 1.70 mPa·s, measured as a 2.0 wt % solution of the esterified cellulose ether in 0.43 wt % aqueous NaOH at 20° C.

5. The esterified cellulose ether of claim 1 wherein the aliphatic monovalent acyl groups are acetyl, propionyl or butyryl groups and the groups of the formula —C(O)—R—COOA are —C(O)—$CH_2$—$CH_2$—COOA, —C(O)—CH=CH—COOA, or —C(O)—$C_6H_4$—COOA groups.

6. The esterified cellulose ether of claim 1 being hydroxypropyl methyl cellulose acetate succinate.

7. A composition comprising a liquid diluent and at least one esterified cellulose ether of claim 1.

8. The composition of claim 7 additionally comprising at least one active ingredient and optionally one or more adjuvants.

9. The composition of claim 7 comprising from 10 to 25 percent of at least one esterified cellulose ether, from 70 to 89, percent of a liquid diluent, and from 1 to 15 percent, of an active ingredient, based on the total weight of the composition.

10. A solid dispersion comprising at least one active ingredient and at least one esterified cellulose ether of claim 1.

11. The solid dispersion of claim 10 wherein the solid dispersion has been formulated into tablets, pills, granules, pellets, caplets, microparticles, fillings of capsules, or into a paste, cream, suspension or slurry.

12. A dosage form being coated with at least one esterified cellulose ether of claim 1.

13. A capsule shell comprising at least one esterified cellulose ether of claim 1.

* * * * *